(12) United States Patent
Pedersen

(10) Patent No.: US 6,607,711 B2
(45) Date of Patent: *Aug. 19, 2003

(54) MOUTH HYGIENIC COMPOSITION FOR THE TREATMENT OF HALITOSIS

(76) Inventor: Ejvind Jersie Pedersen, Ulvshalevej 70, Stege (DK), DK-4780

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/475,122

(22) Filed: Dec. 30, 1999

(65) Prior Publication Data

US 2003/0012744 A1 Jan. 16, 2003

(30) Foreign Application Priority Data

Oct. 7, 1997 (DK) .......................... 1997 01149
Sep. 28, 1998 (WO) ................. PCT/IB98/01503

(51) Int. Cl.$^7$ ............... A61K 7/16; A61K 7/24; A61K 7/22

(52) U.S. Cl. ................ 424/49; 424/54; 514/836; 514/901

(58) Field of Search ..................... 424/54, 49

(56) References Cited

U.S. PATENT DOCUMENTS

| | | | | |
|---|---|---|---|---|
| 3,655,868 A | 4/1972 | Vagenius et a. | ............... | 424/54 |
| 4,314,991 A | 2/1982 | Sipos | ............... | 424/56 |
| 4,339,432 A | 7/1982 | Ritchey et al. | ............... | 424/54 |
| 4,416,867 A | 11/1983 | Ritchey et al. | ............... | 424/49 |
| 4,425,325 A * | 1/1984 | Ritchey et al. | ............... | 424/49 |
| 4,622,220 A | 11/1986 | Frosch | ............... | 424/49 |
| 4,652,444 A | 3/1987 | Maurer | ............... | 424/49 |
| 4,684,528 A | 8/1987 | Godfrey | ............... | 426/74 |
| 4,689,214 A | 8/1987 | Niles et al. | ............... | 424/49 |
| 4,719,100 A | 1/1988 | Frosch | ............... | 424/49 |
| 4,758,439 A | 7/1988 | Godfrey | ............... | 426/74 |
| 4,814,163 A | 3/1989 | Barth | ............... | 424/49 |
| 4,814,164 A | 3/1989 | Barth et al. | ............... | 424/49 |
| 4,830,716 A | 5/1989 | Ashmead | ............... | 204/72 |
| 4,956,385 A | 9/1990 | Eby, III | ............... | 514/494 |
| 4,992,259 A | 2/1991 | Schiraldi et al. | ............... | 424/49 |
| 4,997,640 A | 3/1991 | Bird et al. | ............... | 424/52 |
| 5,002,970 A * | 3/1991 | Eby, III | ............... | 424/439 |
| 5,059,416 A | 10/1991 | Cherukuri et al. | ............ | 424/48 |
| 5,094,842 A | 3/1992 | Riley | ............... | 424/52 |
| 5,332,579 A | 7/1994 | Umbdenstock | ............ | 424/639 |
| 5,358,705 A | 10/1994 | Boggs et al. | ............ | 424/54 |
| 5,405,836 A | 4/1995 | Richar et al. | ............... | 514/23 |
| 5,409,905 A | 4/1995 | Eby, III | ............... | 514/23 |
| 5,500,448 A | 3/1996 | Cummins et al. | ............ | 514/717 |
| 5,504,055 A | 4/1996 | Hsu | ............... | 504/121 |
| 5,516,925 A | 5/1996 | Pedersen et al. | ............... | 556/50 |
| 5,833,952 A | 11/1998 | Grigor et al. | ............... | 424/49 |

FOREIGN PATENT DOCUMENTS

| | | |
|---|---|---|
| CA | 2154860 | 1/1996 |
| EP | 0 251 146 | 1/1988 |
| EP | 0 251 542 | 1/1988 |
| EP | 0 522 965 | 1/1993 |
| EP | 0 658 565 | 6/1995 |
| EP | 0 721 774 | 7/1996 |
| GB | 2 187 642 | 9/1987 |
| JP | 47-37557 | 9/1972 |
| WO | WO86/00004 | 1/1986 |
| WO | WO94/14407 | 7/1994 |
| WO | WO94/26243 | 11/1994 |
| WO | WO94/26244 | 11/1994 |
| WO | WO95/07682 | 3/1995 |
| WO | WO96/05803 | 2/1996 |
| WO | WO96/06099 | 2/1996 |
| WO | WO96/06101 | 2/1996 |

OTHER PUBLICATIONS

Richter, J.L, "Diagnosis and Treatment of Halitosis", Compendium, vol. 17, No. 4, Apr. 1996, pp. 370–386.

Waler, S.M., "The effect of zinc–containing chewing gum on volatile sulfur–containing compounds in the oral cavity", ACTA ODONTOL SCAND, vol. 55, 1997, pp. 198–200.

"Zinc Amino Acid Chelate TF (Taste Free) 10% Zn", Product No. 3463, Product Description Data, Albion Laboratories Inc., Apr. 1995.

* cited by examiner

*Primary Examiner*—Frederick Krass
*Assistant Examiner*—Donna Jagoe
(74) *Attorney, Agent, or Firm*—Jacobson Holman PLLC

(57) ABSTRACT

A mouth hygienic composition effective in treating halitosis. The composition comprises a chelate comprising a metal ion, preferably a zinc ion, and an amino acid, preferably glycine.

28 Claims, 1 Drawing Sheet

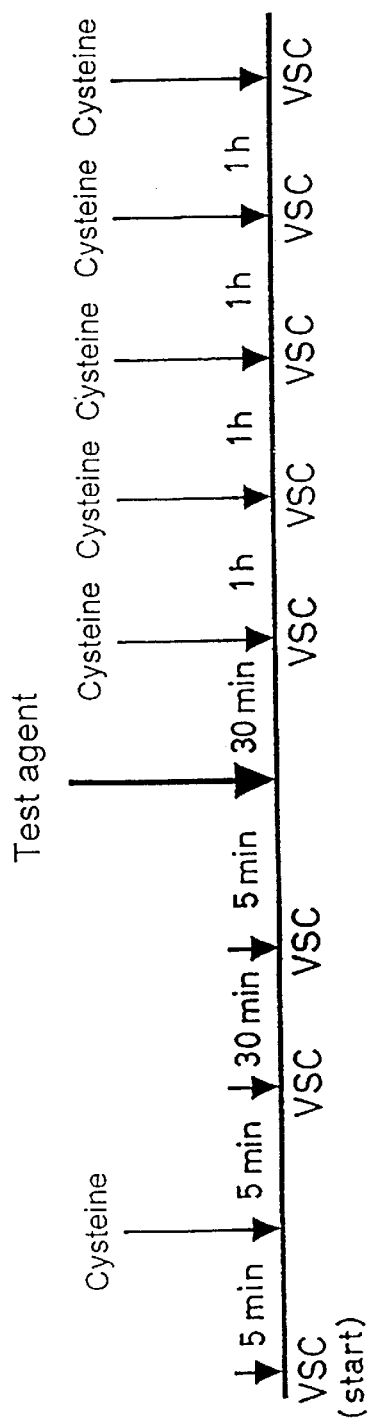
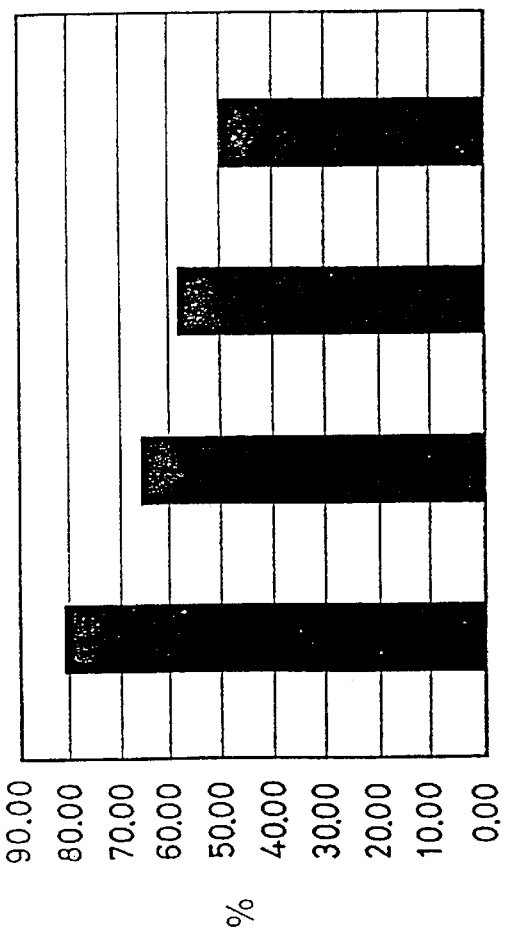

MOUTH HYGIENIC COMPOSITION FOR THE TREATMENT OF HALITOSIS

FIELD OF INVENTION

This invention relates to a mouth hygienic composition, which is useful in preventing or reducing bad breath, in particular for the treatment of halitosis, in the prevention of plaque formation, gingivitis and calculus and thus suitably facilitate the development of a healthy mouth hygiene. It also relates to the use of a particular metal chelate in the composition and a method for using the composition.

BACKGROUND OF THE INVENTION

It is widely accepted that for many people the affliction of halitosis (bad breath) may constitute a serious problem, particularly in social encounters. The breath malodour may be very severe and it may occur e.g. occasionally, regularly, or chronically and at specific times of the day or month. For the purposes of this application, the terms "bad breath", "halitosis" and "breath malodour" all mean an unpleasant breath odour that is objectionable to others.

Public awareness and concern for this phenomenon are evidenced e.g. by the support of an estimated $850 million mouth wash industry in the United States of America, despite reports that commercially available products have no significant effect on breath malodour. Recent public opinion polls (taken between 1994 and 1995) have for example revealed that about 55 to 75 million Americans consider bad breath a principle concern in social encounters (J. L. Richter: Diagnosis and Treatment of Halitosis; Compendium 17 (1996); p. 370–386, and references quoted therein).

Studies on the etiologies of breath malodour agree that hydrogen sulphide ($H_2S$), methyl mercaptan ($CH_3SH$), and dimethyl sulphide ($CH_3SCH_3$), collectively referred to as volatile sulphur compounds (VSC) are the principal odourants in bad breath. Volatile sulphur compounds (VSC) originate from the anaerobic bacterial degradation of sulphur-containing amino acids within the oral cavity. It is now generally accepted that volatile sulphur compounds (VSC) constitute the major component of halitosis or bad breath originating from the oral cavity. It has also been shown that anaerobic, Gram negative bacteria are responsible for this odour production.

Consequently, all conditions which favour the retention of such a microbial flora predispose for the formation of VSC and thereby contribute to the development of halitosis. As substrates for odour production, the bacteria mainly utilize the amino acids methionine and cysteine present in e.g. proteins from a dietary intake. These amino acids contain sulphur and are metabolized by the bacteria to yield volatile sulphur compounds. These substances have an unpleasant odour, even in extremely low concentrations.

DESCRIPTION OF THE PRIOR ART

It is known that aqueous solutions of zinc salts used as mouth rinses reduce and inhibit VSC formation in the oral cavity. It is assumed that zinc ions form stable mercaptides with the substrate, with precursors of VSC or with the VSC directly, since zinc has an affinity for sulphur and oxidizes sulphhydryl groups. It has for example been established that zinc-containing chewing gum has an affect on VSCs in the oral cavity (S. M. Waler: The effect of zinc-containing chewing gum on volatile sulfur-containing compounds in the oral cavity; Acta Odontol. Scand. 55 (1997); p. 198–200).

Several examples of compounds suggested to be effective as halitosis inhibitors are described in the prior art. As an example, Canadian patent application no. 2,154,860 relates to an oral care product which contains alkali metal pyrophosphate and a water-soluble zinc polyamine complex capable of releasing zinc ions in an environment such as the oral cavity. The zinc polyamine complex is formed from a polyamine and a normally water-in-soluble zinc compound such as zinc oxide or zinc citrate. The aim is to provide a high-molecular weight water-soluble polyamine complex of a normally water-insoluble zinc compound which has utility as an ingredient of improved palatability and reduced astringency in oral care products. The water-soluble zinc polyamine complex is present in an aqueous solution which has a clear transparency and is without any visible evidence of a second phase which is distinct from the aqueous phase. Reference is made to the fact that the polyamines cited in the above-mentioned Canadian patent application have an average molecular weight of about 1,500 to 70,000. The invention described in Canadian patent application no. 2,154,860 is significantly different from the present invention, both in terms of the solubility of the zinc compound and in terms of the molecular weight of the composition used.

European patent application no. 0 522 965 A1 discloses a composition for use in the treatment of e.g. halitosis. The composition does not comprise a chelate of an amino acid with a metal ion.

U.S. Pat. No. 4,814,163 relates to a solid antitartar and mouth deodorant composition comprising a physiologically acceptable zinc compound, an ionone ketone terpene derivative, a mint flavour and a sodium or potassium gluconate, and having an acidic pH, in a sugar-free carrier. U.S. Pat. No. 4,814,163 does not disclose a mouth hygienic composition comprising a chelate of a metal ion with an amino acid.

In general, when metals such as zinc, manganese, magnesium, copper, iron, cobalt and others become surrounded by and bonded to amino acids, in a stable form, this is referred to as chelation or chelate formation. Such chelates are referred to in the art as e.g. metal amino acid chelates, mineral amino acid chelates and chelates comprising a metal ion and one or more amino acids. Furthermore, chelates are also often referred to in the art as socalled coordination compounds. The coordination compounds are very often slightly soluble, non-ionic complexes. In the present description, the term "metal amino acid chelate" is used in this meaning.

Chelation is the natural means for the body to transport minerals across the intestinal wall as part of digestion. The body is very efficient at absorbing amino acids in this way. In a priority list of nutritional substances crossing the intestinal wall after digestion, amino acids rank highly. In fact, 95% of all amino acids are absorbed. Chelating minerals such as metal ions to these amino acids facilitates the transport of the mineral across the intestinal wall. In this respect it is very important for the mineral to have a stable bond to the amino acid.

U.S. Pat. No. 5,516,925 relates to mineral amino acid-chelates specifically as supplementary mineral sources for use in human or animal nutrition. It does not relate to a mouth hygienic composition, but is concerned with facilitating the absorption in the gut and mucosal cells of the amino acid chelate.

Water-soluble as well as water-insoluble zinc compounds have also been utilized as physiologically active ingredients in oral care preparations. Water-soluble and highly ionized zinc compounds, such as zinc chloride, would appear to provide a valuable source of bioavailable zinc ions. However, zinc chloride in aqueous solution tends to form oxychloride and zinc hydroxides of low solubility, which results in a two-phase, cloudy solution. The pH of a conventional zinc chloride solution can be lowered to less than 4.5 through the use of mineral or organic acid buffers to provide a stable and clear solution. However, this method is not acceptable since the resultant oral care product exhibits severe astringency and an undesirable sour taste.

Other zinc salts, such as e.g. zinc acetate and zinc citrate, have been used for the prevention of halitosis. However, zinc acetate and zinc citrate also have a high degree of astringency and an undesirable metallic taste. As a consequence of these undesirable characteristics, there has been a long felt need for a zinc-containing compound which is capable of reducing and/or eliminating halitosis. It would be desirable to provide the zinc-containing compound as part of a mouth hygienic composition which dissolves slowly and under controlled conditions in the environment of the oral cavity so as to provide an effective contact between the zinc and the volatile sulphur compounds present in this environment.

SUMMARY OF THE INVENTION

It has now surprisingly been found that various metals, including zinc provided to the oral cavity as part of a metal amino acid chelate, are capable of effectively reducing or eliminating bad or unpleasant breath caused by VSCs. Metal amino acid chelates and in particular certain zinc amino acid chelates do not possess the undesirable metal-like taste and high degree of astringency which are typical of the above-mentioned zinc salts. Therefore the present invention provides an organoleptically acceptable mouth hygienic composition which is effective in the treatment of halitosis and/or bad breath resulting from VSC.

DETAILED DESCRIPTION OF THE INVENTION

The present invention relates in one aspect to a mouth hygienic composition comprising a carrier and a chelate comprising a metal ion moiety and an amino acid moiety. It will be understood that the metal ion can be any metal ion capable of forming a chelate with an amino acid moiety. Preferably, the metal ion is one capable of forming a neutral coordination compound which is relatively non-polar. This is important since it is preferred that the solubility is low in water and generally aqueous environments, such as e.g. the saliva found in the environment of the oral cavity.

In one embodiment, the chelate according to the present invention can exist in aqueous solution up to a concentration of about 2%. At higher concentrations such a chelate becomes colloidal.

The pH of a 1.0% solution of the chelate in distilled water is preferably in the range of 7 to 10, such as in the range of 7.5 to 8.0, for example 8.0 to 8.5, such as 8.5 to 9.0, for example 9.5 to 10.0, such as 7.5 to 9.5, for example 8.0 to 9.0. Furthermore, the chelate can preferably be dispersed in water and will retain its tastefree characteristics in water-based liquids.

Chelates of metal ions with amino acids generally result from the reaction of a metal ion with one or more amino acids. The reaction is guided by e.g. the valence of the metal ion in question and its ability to form so-called "coordination bonds" with the amino group and the carboxy group of the amino acid. Coordination bonds are also known in the art as coordinate covalent bonds.

It is desirable that the reaction leading to the chelate formation takes place under conditions characterized by e.g. a molar ratio such as one mole of metal ion to one to three, preferably two, moles of amino acids. The resulting molecule has two or three five-membered heterocyclic ring structures containing a metal ion attached by coordinate covalent bonds to two or more non-metals in the same molecule. Such chelates differ from traditional salts by having different physical and chemical properties such as e.g. the nature of the chemical bonds involved in forming the different chemical structures.

For the purpose of this invention, a salt is understood to be any compound produced when all or part of the hydrogen of an acid is replaced by an electropositive radical or a metal ion. Salts are usually formed by treating a metal with an acid or by the interaction of a base and an acid.

Accordingly, it should be noted that a chelate is not the same as a complex or, indeed, a complex mixture of a mineral and a protein hydrolysate. Consequently, simply mixing inorganic minerals with amino acids in a liquid or dry mixture does not fall into the category of a true amino acid chelate. Such a simple ionic and hydrogen bonding of minerals to amino acids does not produce a stable product. Special processing must be performed to create a stable (covalent) bond, which is important for greater bioavailability.

In general, organic reagents yielding sparingly soluble coordination compounds typically contain at least two functional groups, each of which is capable of bonding with the metal ion by donation of a pair of electrons. The functional groups are located in the molecule in such a way that the above-mentioned five- or six-membered ring structure results from the chelate formation. Coordination compounds which form complexes of this type are also referred to in the art as chelating agents. When forming a product with e.g. a mineral, such as a metal ion, the complex is termed a chelate.

Neutral coordination compounds are relatively non-polar. As a consequence, their solubilities are low in water. The low degree of solubility of a neutral coordination compound can be exploited e.g. when providing a composition which is to be slowly dissolved in an aqueous environment, such as in the saliva of the oral cavity.

As already mentioned, several definitions of a metal amino acid chelate are available in the art. One such definition is concerned with the molecular weight of the metal amino acid chelate. The molecular weight of the chelate is determined partly by the metal ion and partly by the amino acid moiety. It has been suggested that one such definition should be that a metal amino acid chelate should have a molecular weight of at the most 800 Daltons (g/mol). To determine the molecular weight of a chelate, the atomic weight of all the atoms in the ligands plus the atomic weight of the metal ion being chelated should be included.

For example, one of the heaviest metals normally chelated is molybdenum with an atomic weight of 95.94 Daltons. In its +3 oxidation state, molybdenum can be bonded to three amino acids. Tryptophane is the heaviest amino acid, having a molecular weight of 204.22 Daltons. An amino acid chelate of molybdenum and tryptophane with a 1:3 molar ratio (metal:amino acid) would then have a molecular weight of 708.60 Daltons. This illustrates why the upper limit for a true metal amino acid chelate can be set at 800 Daltons.

A metal amino acid chelate can be formed with one, two or three amino acids. It is generally accepted in the art that it is physically impossible to chelate any more amino acids to the metal ion. Additional amino acids must consequently be bonded to other amino acids, which results in the product no longer being a chelate, as it is no longer a coordination compound of a mineral to an amino acid.

Considering the molecular weight of selected metal ion amino acid chelates according to the present invention, the chelated structure comprising e.g. a zinc ion moiety and two tryptophane amino acid moieties would have the molecular weight 489.81 Daltons.

According to one embodiment of the present invention, it is particularly preferred that the chelate comprises a zinc ion moiety and two lysine moieties. Such a chelate will have a molecular weight of 369.25 Daltons. However, the present invention is not limited to zinc lysine chelates. The present invention comprises chelates of a metal ion to preferably either one, two or three amino acids.

Accordingly, in one preferred embodiment of the invention, the mouth hygienic composition comprises a chelate comprising a metal ion moiety and an amino acid moiety, said chelate having a molecular weight of at the most 800 Daltons, such as at the most 750 Daltons, e.g. 700 Daltons, such as 650 Daltons, e.g. 600 Daltons, such as 550 Daltons, e.g. 500 Daltons, such as 450 Daltons, e.g. 400 Daltons, or such as 350 Daltons.

Consequently, the metal amino acid chelate used in the present invention is significantly different from the compounds described in the prior art in terms of both molecular weight and solubility. This difference may well account for the fact that the chelate according to the present invention is particularly useful in treating, preventing and/or eliminating halitosis while at the same time having pleasant organoleptic qualities and being essentially tastefree in the absence of a flavouring agent.

The chelates used in the present invention may in preferred embodiments exist in solution, i.e. be fully dissolved in an aqueous environment, at concentrations of up to at the most 10%. It may be preferred, however, that the solubility is less than 10%, such as 9%, e.g. 8%, such as 7%, e.g. 6%, such as 5%, e.g. 4%, such as 3%, e.g. 2%, or even less than 2%, such as 1,8%, e.g. 1,6%, such as 1,4%, e.g. 1,2%, or even 1%.

The solubility of the chelate according to the present invention will depend both on the metal ion moiety and on the amino acid moiety employed to form the chelate. The chelate may be dispersed in water and will retain its substantially tastefree characteristics in water-based liquids.

The low degree of solubility of a neutral coordination compound of the present invention can be exploited e.g. when providing a mouth hygienic composition which is to be slowly dissolved in an aqueous environment, such as in the saliva of the oral cavity. It is important that the active ingredient of the composition, the metal ion comprising chelate, may suitably be released under controllable conditions which facilitate an effective interaction of the metal ion, preferably a zinc ion, with the volatile sulphur compounds present in an oral cavity environment. This effective interaction desirably takes place without the generation of any astringent taste or unpleasant smell. Preferably, the composition according to the present invention is substantially tasteless unless deliberately being supplemented with a desirable flavouring agent.

It is preferred that the composition according to invention comprises a chelate characterised by having a molar ratio of metal ion moiety to amino acid moiety which is in the range of 1:1 to 1:3, and preferably 1:2. However, the molar ration may well depend both on the individual metal ion moieties and the individual amino acid moieties employed, and the invention is not limited to the molar ratios stated above.

Chelates which are useful in the present invention are commercially available and can be prepared by following the techniques generally available in the art of chelate preparation. As an example, reference can be made to the method of preparing amino acid chelates disclosed by Ashmead in U.S. Pat. No. 4,830,716.

Metals such as e.g. Ag, Ca, Cu, Fe, Mg, Mn, Zn, Mo, Co, Se, Sn and V are suitably used in the preparation of chelates of metal ions with amino acids. Zn is a particularly useful metal in the context of the present invention, as the zinc ion, $Zn^{2+}$, of the chelate is releasable under controllable conditions in the oral cavity and thus readily available for reacting with volatile sulphur compounds (VSC) and other malodourants.

Any biologically acceptable amino acid can be used in the preparation of metal amino acid chelates according to the present invention. This includes e.g. naturally occurring amino acids, essential amino acids, nutritionally valuable amino acids such as for example glycine, alanine, valine, leucine, isoleucine, serine, threonine, aspartic acid, asparagine, glutamic acid, glutamine, lysine, arginine, cysteine, methionine, phenylalanine, tyrosine, tryptophan, histidine and proline.

Suitable amino acids of the present invention also comprise basic amino acids, acidic amino acids, amino acids with aliphatic side chains, amino acids with aromatic side chains, monoamino-monocarboxylic amino acids, hydroxy-monoamino-monocarboxylic amino acids, monoamino-dicarboxylic amino acids, amidocarboxylic amino acids and diamino-monocarboxylic amino acids. In general, the reactability of both the carboxy group and the amino group of an amino acid with a metal ion moiety facilitates the formation of the chelated structure. This readily explains why almost any biologically acceptable amino acid will most likely be able to facilitate the formation of the chelated structures present in the compositions according to the present invention.

Although any of the above-stated amino acids may contribute to the desirable formation of chelates capable of releasing a metal ion under suitable conditions, lysine is particularly preferred, as compositions comprising this amino acid chelated to a zinc ion have been shown to be exceptionally effective in treating halitosis.

In one particular useful embodiment of the present invention, the mouth hygienic composition comprises a chelate of the general formula

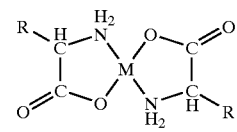

or is an aqueous solvent thereof,
wherein M is a metal ion moiety, preferably, but not limited to, a zinc ion moiety, and R is a side chain of a biologically acceptable amino acid moiety, preferably lysine or an amino acid with similar functional physico-chemical properties as lysine. The side chain R may also include H, in which case the amino acid is glycine.

Accordingly, in one particular interesting embodiment of the invention, the chelate of the present invention comprises an amino acid residue wherein the side chain R has the structure —$CH_2$—$CH_2$—$CH_2$—$CH_2$—$NH_2$ or is a functional derivative hereof. The term functional derivative shall be interpreted to mean that the derivative has similar or substantially similar properties as compared to the non-derivatised side chain.

In addition to chelates comprising $Zn^{2+}$, other useful chelates of amino acids may be formed with either $Ag^{2+}$, $Sn^{2+}$ or $Cu^{2+}$. At present, results clearly demonstrate that $Zn^{2+}$ comprising chelates are particularly useful in treating halitosis.

In one embodiment of the invention, $Zn^{2+}$ is preferably present in the mouth hygienic composition in an amount of 0.05 to 2.0 weight percent, such as 0.1 to 1.9 weight percent, more preferably 0.2 to 1.8 weight percent, such as 0,4 to 1,7 weight percent, even more preferably 0.6 to 1.6 weight percent, such as 0.8 to 1.4 weight percent, and most preferably 1.0 to 1.3 weight percent, such as 1.2 weight percent.

In another embodiment of the present invention, the composition comprises $Zn^{2+}$ in an amount of less than 4.0 weight percent, such as less than 3.0 weight percent, for example less than 2.5 weight percent, such as less than 2.0 weight percent, for example less than 1.5 weight percent, such as less than 1.3 weight percent, for example less than 1.1 weight percent, such as less than 0.9 weight percent, for example less than 0.7 weight percent, such as less than 0.5 weight percent, for example less than 0.3 weight percent, such as less than 0.1 weight percent.

In another useful embodiment of the present invention, the mouth hygienic composition comprises a chelate comprising a biologically acceptable amino acid, said biologically acceptable amino acid having an isoelectric point in the range of pH=8.0 to pH=12, such as the range of pH=9.0 to pH=11.5, for example the range of pH=9.5 to pH=11.0.

In yet another embodiment of the present invention, the mouth hygienic composition comprises a chelate comprising a biologically acceptable amino acid which has an isoelectric point in the range of pH=4.0 to pH=8.0, such as the range of pH=4.5 to pH=7.5, for example the range of pH=5.0 to pH=7.0, such as the range of pH=5.5 to pH=6.5.

The composition of the present invention may be flavoured with a flavouring agent to make it more palatable. Suitable flavouring agents are those generating a flavour of e.g. lemon, strawberry, raspberry, peach, blackcurrent, orange or cherry. Raspberry flavouring agents are particularly preferred due to their ability to provide particularly pleasing organoleptic qualities and their ability to reduce and/or eliminate any traces of an astringent taste associated with the metal amino acid chelate.

It is very important that the composition has desirable organoleptic qualities and is substantially free from any metallic and/or astringent taste. Accordingly, the composition in one particularly useful embodiment is substantially tasteless, i.e. free from any metallic and/or astringent taste.

Apart from being palatable, it is also desirable that the composition is capable of releasing the chelate in an aqueous environment, such as e.g. the oral cavity, under controllable conditions, such as e.g. slowly and/or at a steady rate. To facilitate the formation of such an environment the composition may comprise a saliva-inducing agent such as e.g. sorbitol and/or xylitol in a suitable ratio in order to stimulate the production of saliva in the oral cavity. This stimulation will facilitate the slow and/or controlled release of the chelate from the composition mainly due to the largely insoluble nature of the metal amino acid chelate.

In another aspect of the invention, there is provided a composition for use in the reduction and/or elimination of halitosis. The successful treatment of halitosis will be demonstrated in the practical examples provided below. The composition according to the present invention may also effective for use in the prevention, reduction and/or elimination of plaque formation. This aspect of the invention is largely due to the fact that plaque formation in the oral cavity is due to a microbial growth and activity. However, by reacting with the sulphur-containing amino acids in the oral cavity, the metal ion moiety of the chelate significantly reduces the microbial growth potential which in turn is likely to lead to a reduced plaque formation. Consequently, there is, in effect, also provided a composition for use in oxidizing volatile sulphur compounds (VSC) in the oral cavity.

Additional aspects of the invention relate to the treatment of gingivitis and calculus, relief from garlic odours in the breath following the intake of a garlic-containing diet, or following the intake of tablets containing garlic as e.g. a supplement to an already healthy diet. Garlic odours typically result from dimethyl sulphide.

The composition of the present invention is preferably in the form of a preparation suitable for controlled release of the metal amino acid chelate in the oral cavity. Such a preparation or formulation is suitably a lozenge, a troche, a chewing gum, a toothpaste, a liquid mouth-rinsing composition, a sweet and a resoriblet. A lozenge is particularly preferred.

A toothpaste formulation can be prepared e.g. by blending the mouth hygienic composition or the chelate according to the present invention with a pyrophosphate ingredient, and other conventional ingredients which are employed as adjuvants in oral care products. Suitable alkali metal pyrophosphates include dialkali metal and tetraalkali metal pyrophosphate and mixtures thereof in a hydrated or unhydrated form. Illustrative of pyrophosphate salts are $Na_2H_2P_2O_7$, $Na_4P_2O_7$ and $K_4P_2O_7$.

Suitable adjuvants include whitening agents such as titanium dioxide, preservatives, silicones, chlorophyll compounds, peroxygen compounds such as sodium percarbonate, antimicrobial agents such as cetyl pyridinium chloride, flavourants such as oils of spearmint and peppermint, sweetening agents such as sucrose, xylitol, sorbitol, and sodium cyclamate, fluoride compounds such as sodium fluoride and sodium monofluorophosphate, humectants such as glycerin, gelling agents such as sodium carboxymethylcellulose, abrasives such as alpha-alumina, particulate polyvinyl chloride, calcium phosphate, silica xerogel and sodium bicarbonate, and the like.

Other adjuvants employed in toothpaste formulations include between 0.05 to 5 parts by weight of a surfactant such as cetyltrimethylammonium bromide, sodium lauryl sulfate, sodium dodecylbenzenesulfonate, ammonium lignosulfonate, condensation products of ethylene oxide with fatty alcohols, amines or alkylphenols, partial esters of fatty acids and hexitol anhydrides, and the like.

In one particularly preferred embodiment, the composition or the chelate according to the present invention is comprised in a toothpaste formulation preferably comprising sorbitol, hydrated silica, PEG-32 (polyethylene glycol), sodium lauryl sulfate, aroma and/or flavouring agents, titan dioxide, sodium fluoride, potassium sorbate, sodium saccharin, cellulose gum and trisodium phosphate.

A mouthwash formulation comprising the mouth hygienic composition or the chelate according to the, present invention can be prepared by blending the composition or the chelate with suitable ingredients such as e.g. those described above, and such as aqueous ethanol, glycerin, sorbitol, surfactant, colourant, flavourant, antimicrobial agents, and the like.

A tablet, preferably a lozenge or a troche, can be prepared by blending the mouth hygienic composition or the chelate of the present invention with conventional ingredients routinely used for the preparation of tablets and/or lozenges. Such ingredients comprise e.g. sorbitol, xylitol, sucrose, fructose, hydrolysed starch, magnesium stearate, a flavouring agent, a binding agent, a sweetener, a gelling agent, an abrasive, and the like, such as the e.g. the ingredients listed above. The lozenge can be prepared according to established procedures and lozenge preparations traditionally used in the art for the preparation of tablets and/or lozenges. In one preferable embodiment, the preparations described above do not contain sugar so as to eliminate the risk of causing calculus and caries.

A chewing gum formulation comprising the mouth hygienic composition or the chelate according to the present invention can be prepared by a person skilled in the art by blending the mouth hygienic composition or the metal amino acid chelate with suitable ingredients such as e.g. those described above, and such as e.g. saccharose, fructose, sorbitol, xylitol, gum bases, resins, polymers, parafins, waxes, glycerin, sorbitol, surfactant, colourant, flavourant, antimicrobial agents and the like.

According to the present invention there is also provided a method of reducing and/or eliminating halitosis by means of oral administration to the oral cavity of the composition according to the present invention.

A socalled Halimeter may be used for testing the mouth hygienic effects of composition and the chelate comprised herein. The "cysteine challenge method" is suitably used for this form of testing. Consequently, after initial measurement of a VSC base-line value, a mouthwash or rinse is performed with a cysteine solution (6 mM, pH=7.2), and the VLC value is measured again. After approximately 30 minutes the potential halitosis inhibitor is tested. The test takes place in the form of an oral administration of the inhibitor in a suitable form. Repeated mouthwashes at suitable time points after the administration make it possible to test the effect of the potential halitosis inhibitor over time, as indicated in FIG. 1 outlining the experimental model used in the present study.

By using the cysteine challenge method it was possible to test the inhibitory effect of the mouth hygienic composition of the present invention. It was found that an average reduction of VSC production of almost 50% was observed after three hours. Importantly however, immediately after intake of the tablet, a reduction in VSC of more than 80% was measured. One hour after intake of the tablet, a reduction of more than 65% was observed. After two hours, a reduction in the amount of VSC of 56% was measured. The experimental results are listed in Table 3, and the percentage reduction of VSC is illustrated in FIG. 2.

It is clear from the results that the mouth hygienic composition of the present invention is capable of significantly reducing VSC in the oral cavity. It should also be noted that the cysteine challenge method is a very harsh method since it initially generates VSC in an amount of around 1000 ppb. This level corresponds to a very severe bad breath. It is therefore remarkable that a reduction of more than 80% is observed immediately after intake of the mouth hygienic composition of the present invention, as illustrated in Table 3. The reduction of more than 80% is remarkable in so far as the traditional treatment of halitosis has in many cases only been able to generate reductions of 40% to 50% in the concentration of VSC.

In another embodiment of the invention there is provided a method comprising the steps of i) oral administration of the composition to the oral cavity,
ii) allowing the composition to be in contact with volatile sulphur-containing compounds of the oral cavity for at least 30 seconds.

A socalled Halimeter is an instrument widely used in the field of halitosis research and treatment, which quantifies breath measurement in parts per billion (ppb) of volatile sulphur compounds (VSC). The ability of the Halimeter to measure VSC is based on the fact that the Halimeter is initially calibrated with an accurately known sulphide gas standard. Because of the ability of the Halimeter to quantify VSC concentrations at the parts per billion level, these instruments have been used in academic studies of halitosis. The Halimeter gives a digital read-out in parts per billion, which is not only quantitative, but also more accurate than the subjective organoleptic methods also used in the art. The Halimeter is specifically designed to serve as a reliable monitor for the measurement of VSC concentrations. The Halimeter used for measuring VSC concentrations were used according to the instructions provided by the manufacturer.

The Halimeter consists of a sensing device and a pump to draw the oral sample through the sensor. The sensing device is a highly sensitive electrochemical voltametric sensor which generates a signal when exposed to sulphide and mercaptane gases The result of the Halimeter measurement can easily be compared to a standard curve or to the peak values regarded as normal and acceptable levels of VSC, which are generally regarded not to constitute a bad breath problem.

Dental practitioners and researchers generally consider peak values of less than 150 to 200 ppb as normal levels of VSC. Such levels of VSC are not normally associated with bad breath problems. It has been reported that, based on Halimeter data of several hundred patients, the average range of bad breath readings is 300 to 500 ppb, although levels as high as 1000 ppb have been encountered.

The so-called "cysteine challenge method" was used in order to test the effectiveness of the mouth hygienic composition of the present invention in the treatment of halitosis. The cysteine challenge method is a standardized method routinely used for the analysis of potential inhibitors of halitosis. The method is based on the fact that repeated mouthwashes with an aqueous cysteine solution result in a significantly increased VSC production. This, in effect, simulates halitosis and makes it possible to test a potential inhibitor hereof.

Following oral administration of the composition it is possible by halimetric determination to directly measure the reduction in the concentration of VSC in the breath. It is preferred that the amount of VSC detectable after oral administration of the composition is reduced at least 50%, preferably at least 60%, even more preferably at least 70%, such as at least 80%, and most preferably at least 90%, such as at least 95%, as compared to the amount of VSCs detectable prior to the oral administration of the composition. In a particularly preferred embodiment of this method, the composition is administered as a lozenge.

In yet another aspect of the present invention there is provided the use of a chelate comprising a metal ion moiety and an amino acid moiety as a component of a composition for the treatment of halitosis and/or in the prevention of plaque formation. Additional uses of such a chelate is in the prevention and/or treatment of gingivitis and calculus. The chelate used in this way may preferably have a molar ratio of a metal ion moiety to a amino acid moiety of 1:1 to 1:3, even more preferably a moiety of 1:2.

In one preferred embodiment there is provided the use of a chelate having the general formula

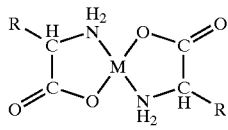

wherein M is a metal ion and R is a side chain of a biologically acceptable amino acid including H, in which case the amino acid is glycine. The metal ion M is preferably selected from the group consisting of $Ag^{2+}$, $Zn^{2+}$, $Sn^{2+}$ and $Cu^{2+}$. $Zn^{2+}$ is particularly preferred.

When $Zn^{2+}$ is the metal ion moiety, it is preferably present in an amount of 0.05 to 2.0 weight percent, such as 0.1 to 1.9 weight percent, more preferably 0.2 to 1.8 weight percent, such as 0,4 to 1,7 weight percent, even more preferably 0.6 to 1.6 weight percent, such as 0.8 to 1.4 weight percent, and most preferably 1.0 to 1.3 weight percent, such as 1.2 weight percent. In another embodiment the zinc ion of the chelate of the present invention is preferably present in an amount of less than 4.0 weight percent, such as less than 3.0 weight percent, for example less than 2.5 weight percent, such as less than 2.0 weight percent, for example less than 1.5 weight percent, such as less than 1.3 weight percent, for example less than 1.1 weight percent, such as less than 0.9 weight percent, for example less than 0.7 weight percent, such as less than 0.5 weight percent, for example less than 0.3 weight percent, such as less than 0.1 weight percent.

There is also provided the use of a chelate according to the invention wherein the amino acid moiety is a naturally occurring amino acid, such as e.g. an essential amino acid, such as e.g. a basic amino acid, such as e.g. glycine or lysine or a functional derivative hereof, such as e.g. functional derivatives having an altered side chain albeit similar or substantially similar physico-chemical properties.

There is also provided the use of a chelate wherein the biologically acceptable amino acid present herein preferably has an isoelectric point in the range of pH=8.0 to pH=12, such as the range of pH=9.0 to pH=11.5, for example the range of pH=9.5 to pH=11.0. In one particularly preferred embodiment, this biologically acceptable amino acid is a diamino-monocarboxylic acid, or a monoamino-monocarboxylic acid.

In yet another preferred embodiment of the invention there is provided the use of a metal amino acid chelate for binding volatile sulphur compounds (VSC) in the oral cavity.

EXAMPLES

The following examples illustrate the invention. Although the components and the specific ingredients are presented as being typical, various modifications within the scope of the invention as defined by the appended claims can be made.

Example 1

It was initially decided to analyse various zinc-containing compounds for their ability to reduce and/or eliminate halitosis. The zinc-compounds are listed in Table 1 below.

TABLE 1

Zinc-compounds analysed for their inhibitory effect on halitosis. The solubility is calculated as the amount in grams of the compound which can be dissolved per gram solvent ($H^2O$).

| Compound | Source | Solubility (g/g $H_2O$) |
|---|---|---|
| Zinc acetate | Merck Index | 0.43 |
| Zinc chloride | Merck Index | 4.3 |
| Zinc citrate | Merck Index | <0.1 |
| $ZnSO_4(H_2O)_6$ | Merck Index | 1.7 |
| Zinc gluconate | Martindale Akzo | 0.12 |
| Zinc amino acid chelate, TF | Albion Lab. | 0.02 |

More than 16 different experiments were carried out with these compounds. With the exception of the zinc amino acid chelate TF (tastefree) 10% Zn, product no. 3463, (Albion Laboratories, Inc., Clearfield, Utah 84015, USA), zinc acetate, zinc chloride, zinc citrate, $ZnSO_4(H_2O)_6$ and zinc gluconate all had very poor organoleptic qualities, particularly a pronounced metallic taste, effectively preventing these compounds from being used commercially as an effective inhibitor of halitosis. It was not possible to find a way in which to reduce or eliminate this metallic taste.

It was generally found that a treatment for halitosis was most effective when a high concentration of Zn was employed and when the zinc compound had a high degree of solubility.

The results obtained by using the zinc amino acid chelate TF (product no. 3463 from Albion Laboratories) was, however, very encouraging, as the results showed that this compound was able to reduce VSC to a degree comparable to the reduction observed when using zinc gluconate. Importantly, the zinc amino acid chelate TF was substantially tastefree and thus an ideal candidate for an effective inhibitor of halitosis. It was subsequently decided to analyse the effect of the zinc amino acid chelate on halitosis more thoroughly.

Example 2

The below Table shows the ingredients used for preparing a lozenge, which was subsequently used in a "cysteine challenge test" in order to analyse its effectiveness in inhibiting halitosis. The zinc amino acid chelate was initially granulated with P.V.P. in isopropanol according to standard procedures. Xylitol was dried at 35° C. and added to the granulate along with the other ingredients in the amounts indicated in the Table. The lozenge produced in accordance with standard preparation techniques had a weight of approximately 0.5 g.

TABLE 2

Ingredients used in preparing 100,000 lozenges for inhibiting halitosis according to the present invention.

| Ingredient | Amount |
|---|---|
| zinc amino acid chelate TF (Albion Labs. no. 3463) | 6800 g |
| Polyvinylpyrrolidone | 800 g |
| Xylitol | 10.576 g |
| Sorbitol | 39.650 g |
| Talcum | 4.550 g |
| Saccharin sodium | 170 g |
| Raspberry flavouring agent | 1.665 g |
| Mg stearate | 250 g |

The lozenge was used in a "cysteine challenge test", and volatile sulphur compounds were detected by using a Halimeter, as described in the below Example 3.

Example 3

The use of a Halimeter for testing the mouth hygienic effects of the lozenge having the composition as described in Example 2 showed that the lozenge is remarkably effective in reducing and inhibiting halitosis.

After initial measurement of a VSC base-line value, a mouthwash or rinse was performed with a cysteine solution (6 mM, pH=7.2), and the VSC value was again measured. After approximately 30–40 minutes the lozenge was administered to the oral cavity, and the VSC value was measured immediately after this administration.

Repeated mouthwashes at suitable time points after the administration, as indicated in Table 3 and FIG. 1, facilitated the analysis of the effect of the lozenge as an effective inhibitor of Halitosis.

TABLE 3

TREATMENT WITH TABLET X

|   | ppb VSC Basis | ppb VSC Cysteine | ppb VSC Tablet X | ppb VSC Cysteine | % reduction after treatment | ppb VSC + 1 h Cysteine | % reduction after 1 h | ppb VSC + 2 h Cysteine | % reduction after 2 h | ppb VSC after + 3 h Cysteine | % reduction after 3 h |
|---|---|---|---|---|---|---|---|---|---|---|---|
| A | 230 | 1165 | 252 | 300 | 74.25 | 521 | 55.28 | 613 | 47.38 | 647 | 44.46 |
| S | 265 | 2600 | 270 | 288 | 88.92 | 840 | 67.69 | 1112 | 57.23 | 1470 | 43.46 |
| G | 250 | 1043 | 248 | 266 | 74.50 | 390 | 62.61 | 489 | 53.12 | 620 | 40.56 |
| SM | 189 | 1472 | 159 | 172 | 88.32 | 450 | 69.43 | 604 | 58.97 | 545 | 62.98 |
| SJ | 291 | 1500 | 279 | 330 | 78.00 | 400 | 73.33 | 546 | 63.60 | 635 | 57.67 |
| Average | 245 | 1556 | 241.6 | 271.2 | 80.80 | 520.2 | 65.67 | 672.8 | 56.06 | 783.4 | 49.82 |
| max | 291 | 2600 | 279 | 330 | 88.92 | 840 | 73.33 | 1112 | 63.6 | 1470 | 62.98 |
| min | 189 | 1043 | 158 | 172 | 74.25 | 390 | 55.28 | 489 | 47.38 | 545 | 40.56 |

The results show that an average reduction of VSC production of almost 50% was observed three hours after administration of the lozenge. Importantly however, immediately after intake of the lozenge, a reduction in VSC of more than 80% was measured. One hour after intake of the lozenge, a reduction of more than 65% was observed. After two hours, a reduction in the amount of VSC of 56% was measured. The experimental results are listed in Table 3, and the percentage reduction of VSC measured by the Halimeter is illustrated in FIG. 2.

It is clear from the results that the mouth hygienic composition of the present invention is capable of significantly reducing VSC in the oral cavity. It should also be noted that the cysteine challenge method is a very harsh method since it initially generates an amount of VSC of around 1000 ppb. This level corresponds to a very severe bad breath. It is therefore remarkable that a reduction of more than 80% is observed immediately after intake of the mouth hygienic composition of the present invention, as illustrated in Table 3. The reduction of more than 80% is remarkable in so far as the traditional treatment of halitosis has, in many cases, only generated VSC reductions of 40% to 50%.

Example 4

One preferred chewing gum preparation according to the invention is illustrated in Table 4.

TABLE 4

Composition of a new zinc-containing chewing gum preparation

| Product: | Zinc chewing gum |
|---|---|
| Batch number: | test 519/1 |
| Specification | 30% gum base |
|  | 30% sorbitol |
|  | 28% lactytol |
|  | 3.7% anti-caking |
|  | 2% flavour |
|  | 0.3% aspartame |
|  | 5% zinc / 1% citric acid |

LITERATURE REFERENCES

Canadian patent application no. 2,154,860
U.S. Pat. No. 4,814,163
U.S. Pat. No. 5,516,925
EP-0 522 961 A1

J. L. Richter: Diagnosis and Treatment of Halitosis; Compendium 17 (1996); p. 370–386.

S. M. Waler: The effect of zinc-containing chewing gum on volatile sulfur-containing compounds in the oral cavity; Acta Odontol. Scand. 55 (1997); p. 198–200.

What is claimed is:

1. A composition in the form of a preparation effective in the treatment of halitosis, said preparation comprising i) a chelate comprising a metal ion and an amino acid and having the formula

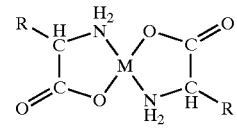

wherein M is a metal ion, which forms coordination bonds with the amino group and with the carboxy group of the amino acid, and R is H or a side chain of a biologically acceptable amino acid, said chelate being controllably releasable into the oral cavity of a subject, ii) a saliva-inducing agent, said saliva-inducing agent being effective in producing saliva in said oral cavity, said saliva-inducing agent being further effective in stimulating a controlled release of said chelate into said oral cavity, iii) a flavouring agent, said flavouring agent being effective in reducing and/or eliminating any trace of an astringent taste associated with said chelate, and iv) a pharmaceutically acceptable carrier.

2. The composition according to claim 1, wherein the metal ion M is selected from the group consisting of $Zn^{2+}$, $Sn^{2+}$, $Cu^{2+}$ and $Ag^{2+}$.

3. The composition according to claim 1, wherein the metal ion M is $Zn^{2+}$.

4. The composition according to claim 3, wherein $Zn^{2+}$ is present in an amount of from 0.05 to 2.0 weight percent.

5. The composition according to claim 1, wherein the biologically acceptable amino acid is a monoamino-monocarboxylic acid.

6. The composition according to claim 5, wherein the monoamino-monocarboxylic acid is glycine.

7. The composition according to claim 1 for use in binding volatile sulphur compounds (VSC) in the oral cavity.

8. The composition according to claim 1, wherein the preparation is a member selected from the group consisting of a lozenge, a chewing gum, a tooth paste and a liquid mouth rinsing composition.

9. The composition according to claim 8, wherein the preparation is a lozenge.

10. A method of reducing and/or eliminating halitosis by means of oral administration to the oral cavity of the composition according to claim 1.

11. The method according to claim 10, said method comprising the steps of
i) oral administration of the composition to the oral cavity,
ii) allowing the composition to be in contact with volatile sulphur-containing compounds of the oral cavity for at least 30 seconds.

12. A method according to claim 10, wherein the amount of volatile sulphur compounds detectable after oral administration of the composition is reduced at least 50% as compared to the amount of volatile sulphur compounds detectable prior to the oral administration of the composition.

13. A method of claim 10, wherein the preparation is a member selected from the group consisting of a lozenge, a chewing gum, a tooth paste and a liquid mouth-rinsing composition.

14. The method of claim 13, wherein the composition is a lozenge.

15. A method of oxidizing volatile sulphur compounds in the oral cavity of a subject, said method comprising the steps of
i) oral administration of the composition according to claim 1 to the oral cavity,
ii) allowing the composition to be in contact with volatile sulphur-containing compounds of the oral cavity for at least 30 seconds.

16. A method according to claim 15, wherein the amount of volatile sulphur compounds detectable after oral administration of the composition is reduced at least 50% as compared to the amount of volatile sulphur compounds detectable prior to the oral administration of the composition.

17. A method for treating halitosis and/or for binding volatile sulphur compounds (VSC) in the oral cavity of a subject, which comprises the steps of:
i. orally administering a composition to the oral cavity of a subject in need of such treatment;
ii. allowing the composition to be in contact with volatile sulphur containing compounds of the oral cavity for at least 30 seconds;
wherein a component of the composition is a chelate of the formula

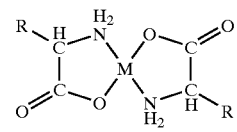

wherein M is a metal ion, which forms coordination bonds with the amino group and with the carboxy group of the amino acid, and R is H or a side chain of a biologically acceptable amino acid.

18. A method according to claim 17 for binding volatile sulphur compounds (VSC) in the oral cavity of a subject.

19. A method according to claim 17, wherein said chelate is controllably releasable into the oral cavity of a subject.

20. A method according to claim 17, wherein the composition further comprises a saliva-inducing agent, said saliva-inducing agent being effective in producing saliva in said oral cavity, said saliva-inducing agent being further effective in stimulating a controlled release of said chelate into said oral cavity.

21. A method according to claim 17, wherein the composition further comprises a flavouring agent, said flavouring agent being effective in reducing and/or eliminating any trace of an astringent taste associated with said chelate.

22. A method according to claim 17, wherein the composition further comprises a pharmaceutically acceptable carrier.

23. A method according to claim 17, wherein the metal ion M is selected from the group consisting of $Zn^{2+}$, $Sn^{2+}$, $Cu^{2+}$ and $Ag^{2+}$.

24. A method according to claim 17, wherein the metal ion M is $Zn^{2+}$.

25. A method according to claim 17, wherein the amino acid is a monoamino-monocarboxylic acid.

26. A method according to claim 25, wherein the monoamino-monocarboxylic acid is glycine.

27. A method according to claim 17, wherein the composition is in the form of a member selected from the group consisting of a lozenge, a chewing gum, a tooth paste and a liquid mouth-rinsing composition.

28. A method according to claim 27, wherein the composition is in the form of a lozenge.

* * * * *